US009408588B2

(12) United States Patent
Huang

(10) Patent No.: US 9,408,588 B2
(45) Date of Patent: Aug. 9, 2016

(54) CMUT PACKAGING FOR ULTRASOUND SYSTEM

(75) Inventor: Yongli Huang, San Jose, CA (US)

(73) Assignee: KOLO TECHNOLOGIES, INC., San Jose, CA (US)

( * ) Notice: Subject to any disclaimer, the term of this patent is extended or adjusted under 35 U.S.C. 154(b) by 1150 days.

(21) Appl. No.: 12/745,754

(22) PCT Filed: Dec. 3, 2008

(86) PCT No.: PCT/US2008/085447
§ 371 (c)(1),
(2), (4) Date: Jun. 2, 2010

(87) PCT Pub. No.: WO2009/073753
PCT Pub. Date: Jun. 11, 2009

(65) Prior Publication Data

US 2010/0280388 A1 Nov. 4, 2010

Related U.S. Application Data

(60) Provisional application No. 60/992,020, filed on Dec. 3, 2007, provisional application No. 61/024,843, filed on Jan. 30, 2008.

(51) Int. Cl.
*H01L 41/00* (2013.01)
*A61B 8/12* (2006.01)
(Continued)

(52) U.S. Cl.
CPC .......... *A61B 8/12* (2013.01); *A61B 8/4483* (2013.01); *B06B 1/0292* (2013.01); *A61B 8/445* (2013.01);
(Continued)

(58) Field of Classification Search
CPC .......... B06B 1/065; B06B 11/00; B06B 3/00; A61B 8/12; H04R 31/00
USPC .......... 600/459, 439, 457, 462, 466; 310/334; 438/48; 73/861.27; 367/181; 257/296, 257/668
See application file for complete search history.

(56) References Cited

U.S. PATENT DOCUMENTS 4,413,520 A 11/1983 Murakami et al.
4,603,589 A 8/1986 Machida
(Continued)

FOREIGN PATENT DOCUMENTS

JP 10192281 7/1998
JP 11501245 2/1999
(Continued)

OTHER PUBLICATIONS

Translated Chinese Office Action mailed Nov. 30, 2011 for Chinese patent application No. 200880117507.8, a counterpart foreign application of U.S. Appl. No. 12/745,758, 18 pages.
(Continued)

*Primary Examiner* — Vani Gupta
(74) *Attorney, Agent, or Firm* — Mattingly & Malur, PC

(57) ABSTRACT

Ultrasonic scanners and methods of manufacturing ultrasonic scanners. One embodiment of a method includes integrating a flexible electronic device (e.g. an IC) and a flexible ultrasonic transducer (e.g. a portion of a circular CMUT array) with a flexible member. The IC, the transducer, and the flexible member can form a flexible subassembly which is rolled up to form an ultrasonic scanner. The integration of the IC and the transducer can occur at the same time. In the alternative, the integration of the electronic device can occur before the integration of the transducer. Moreover, the integration of the transducer can include using a semiconductor technique. Furthermore, the rolled up subassembly can form a lumen or can be attached to a lumen. The method can include folding a portion of the flexible subassembly to form a forward looking transducer. The flexible member of some subassemblies can include a pair of arms.

33 Claims, 12 Drawing Sheets

108
109
120
130
110
136

(51) Int. Cl.
*A61B 8/00* (2006.01)
*B06B 1/02* (2006.01)
*B06B 1/06* (2006.01)
*B06B 3/00* (2006.01)
*H04R 31/00* (2006.01)

(52) U.S. Cl.
CPC ............. *A61B 8/4488* (2013.01); *B06B 1/0651* (2013.01); *B06B 3/00* (2013.01); *H04R 31/00* (2013.01); *Y10T 29/49005* (2015.01)

(56) References Cited

U.S. PATENT DOCUMENTS

| | | | | |
|---|---|---|---|---|
| 5,488,954 | A * | 2/1996 | Sleva et al. | 600/459 |
| 5,870,351 | A | 2/1999 | Ladabaum et al. | |
| 5,872,536 | A | 2/1999 | Lyons et al. | |
| 5,906,580 | A | 5/1999 | Kline-Schoder et al. | |
| 5,957,851 | A | 9/1999 | Hossack | |
| 6,493,288 | B2 | 12/2002 | Khuri-Yakub et al. | |
| 6,558,330 | B1 | 5/2003 | Ayter et al. | |
| 6,558,331 | B1 | 5/2003 | Davidsen et al. | |
| 6,632,178 | B1 * | 10/2003 | Fraser | 600/459 |
| 6,709,392 | B1 | 3/2004 | Salgo et al. | |
| 6,776,763 | B2 | 8/2004 | Nix et al. | |
| 6,854,338 | B2 | 2/2005 | Khuri-Yakub et al. | |
| 6,945,115 | B1 | 9/2005 | Wang | |
| 6,958,255 | B2 | 10/2005 | Khuri-Yakub et al. | |
| 7,212,787 | B2 | 5/2007 | Wu et al. | |
| 7,213,468 | B2 | 5/2007 | Fujimoto | |
| 7,305,883 | B2 | 12/2007 | Khuri-Yakub et al. | |
| 7,408,283 | B2 | 8/2008 | Smith et al. | |
| 7,880,565 | B2 | 2/2011 | Huang | |
| 8,018,301 | B2 | 9/2011 | Huang | |
| 2002/0083771 | A1 | 7/2002 | Khuri-Yakub et al. | |
| 2002/0087083 | A1 | 7/2002 | Nix et al. | |
| 2003/0236443 | A1 | 12/2003 | Cespedes et al. | |
| 2004/0085858 | A1 | 5/2004 | Khuri-Yakub et al. | |
| 2004/0229830 | A1 | 11/2004 | Tachibana et al. | |
| 2005/0004466 | A1 | 1/2005 | Hynynen et al. | |
| 2005/0015009 | A1 | 1/2005 | Mourad et al. | |
| 2005/0137812 | A1 | 6/2005 | Schaffer et al. | |
| 2005/0177045 | A1 | 8/2005 | Degertekin et al. | |
| 2005/0197574 | A1 * | 9/2005 | Eberle et al. | 600/437 |
| 2005/0288873 | A1 | 12/2005 | Urdaneta et al. | |
| 2006/0004289 | A1 | 1/2006 | Tian et al. | |
| 2006/0084875 | A1 | 4/2006 | Knight | |
| 2006/0229659 | A1 | 10/2006 | Gifford et al. | |
| 2007/0013269 | A1 | 1/2007 | Huang | |
| 2007/0066902 | A1 | 3/2007 | Wilser et al. | |
| 2007/0093702 | A1 | 4/2007 | Yu et al. | |
| 2007/0096181 | A1 * | 5/2007 | Lien | 257/296 |
| 2007/0153632 | A1 * | 7/2007 | Chang et al. | 367/181 |
| 2007/0167812 | A1 * | 7/2007 | Lemmerhirt | B06B 1/0292 600/459 |
| 2009/0219743 | A1 * | 9/2009 | Leedy | 365/51 |
| 2010/0013574 | A1 | 1/2010 | Huang | |
| 2010/0160786 | A1 | 6/2010 | Nordgren et al. | |
| 2011/0136284 | A1 | 6/2011 | Huang | |

FOREIGN PATENT DOCUMENTS

| | | |
|---|---|---|
| JP | 2004130136 | 4/2004 |
| JP | 2004337320 | 12/2004 |
| JP | 2004350701 | 12/2004 |
| JP | 2005052342 | 3/2005 |
| JP | 2006122188 | 5/2006 |
| JP | 2006166443 | 6/2006 |
| JP | 2006516368 | 6/2006 |
| JP | 2007130357 | 5/2007 |
| JP | 2007152101 | 6/2007 |
| JP | 2007229328 | 9/2007 |
| JP | 2007244638 | 9/2007 |
| JP | 2007251505 | 9/2007 |
| JP | 2007528153 | 10/2007 |
| JP | 2007307188 | 11/2007 |
| JP | 2008516683 | 5/2008 |
| JP | 2008546239 | 12/2008 |
| WO | WO2005120130 | 12/2005 |
| WO | WO2005120360 | 12/2005 |
| WO | WO2006093913 | 9/2006 |

OTHER PUBLICATIONS

Non-Final Office Action for U.S. Appl. No. 12/326,769, mailed on Jun. 22, 2011, Yongli Huang, "Telemetric Sensing Using Micromachined Ultrasonic Transducer", 7 pages.

Translated Chinese Office Action mailed Jan. 18, 2012 for Chinese patent application No. 2008801174821, a counterpart foreign application of U.S. Appl. No. 60/992,020, 14 pages.

Non-Final Office Action for U.S. Appl. No. 12/745,754, mailed on Mar. 23, 2012, Yongli Huang, "CMUT Packaging for Ultrasound System", 12 pages.

Savoia et al., "Multilayer cMUT Structure for Improved Sensitivity and Bandwidth", 2006 IEEE Ultrasonics Symposium, pp. 1939-1942.

Translated Chinese Office Action mailed Oct. 31, 2012 for Chinese patent application No. 200880117482.1, a counterpart foreign application of U.S. Appl. No. 12/745,754, 9 pages.

Translated Chinese Office Action mailed Jul. 25, 2012 for Chinese patent application No. 200880117507.8, a counterpart foreign application of U.S. Appl. No. 12/745,758, 11 pages.

Translated Chinese Office Action mailed Aug. 24, 2012 for Chinese patent application No. 200880117483.6, a counterpart foreign application of U.S. Appl. No. 12/745,758, 29 pages.

Office action for U.S. Appl. No. 12/326,769, mailed on Dec. 9, 2011, Huang, "Telemetric Sensing Using Micromachined Ultrasonic Transducer", 8 pages.

Final Office Action for U.S. Appl. No. 12/326,769, mailed on Jul. 24, 2012, Yongli Huang, "Telemetric Sensing Using Micromachined Ultrasonic Transducer", 7 pages.

Translated Chinese Office Action mailed Mar. 1, 2013 for Chinese patent application No. 200880117507.8, a counterpart foreign application of U.S. Appl. No. 12/745,758, 8 pages.

Translated Chinese Office Action mailed Apr. 26, 2013 for Chinese patent application No. 200880117482.1, a counterpart foreign application of U.S. Appl. No. 12/745,754, 7 pages.

Japanese Office Action mailed Jun. 14, 2013 for Japanese patent application No. 2010-536240, a counterpart foreign application of U.S. Appl. No. 12/745,758, 9 pages.

Translated Japanese Office Action mailed Jun. 14, 2013 for Japanese patent application No. 2010-536241, a counterpart foreign application of U.S. Appl. No. 12/745,754, 9 pages.

Translated Japanese Office Action mailed Jul. 5, 2013 for Japanese patent application No. 2010-536239, a counterpart foreign application of U.S. Appl. No. 12/745,754, 8 pages.

Non-Final Office Action for U.S. Appl. No. 12/745,758, mailed on May 7, 2013, Yongli Huang, "Ultrasound Scanner Built with Capacitive Micromachined Ultrasonic Transducers (CMUTS)", 18 pages.

* cited by examiner

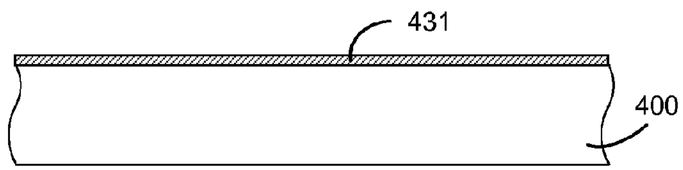
FIG. 4.1
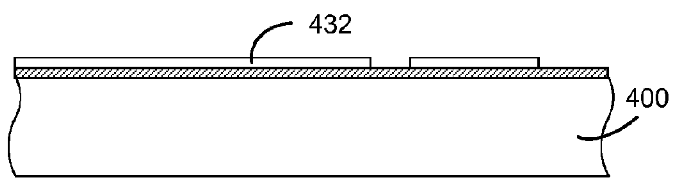
FIG. 4.2
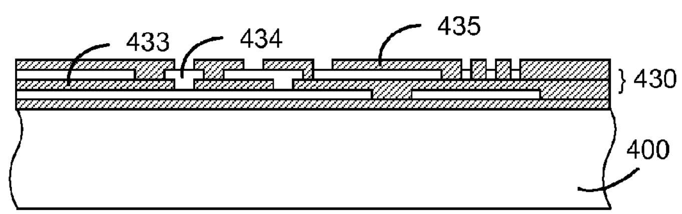
FIG. 4.3
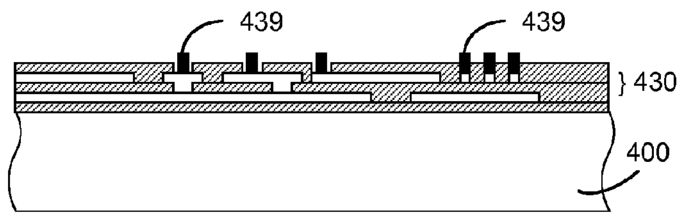
FIG. 4.4
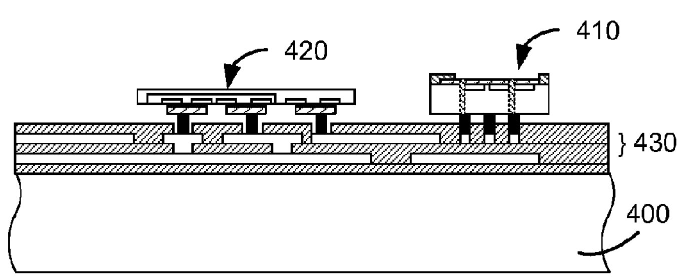
FIG. 4.5
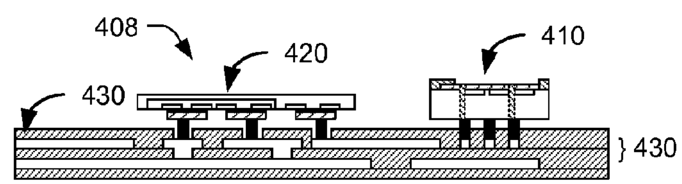
FIG. 4.6

FIG. 5.1
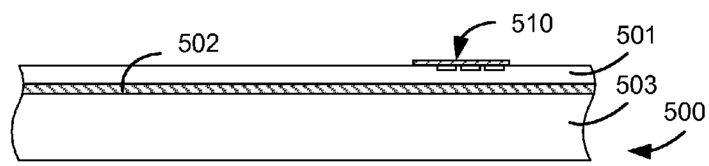
FIG. 5.2
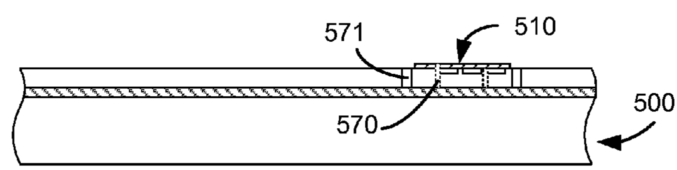
FIG. 5.3
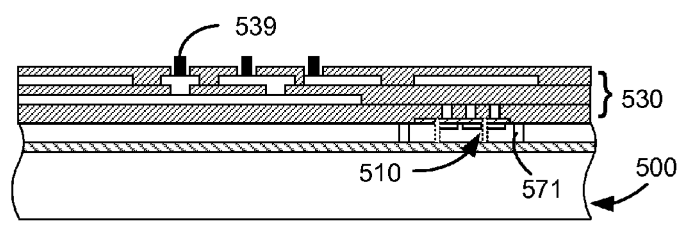
FIG. 5.4
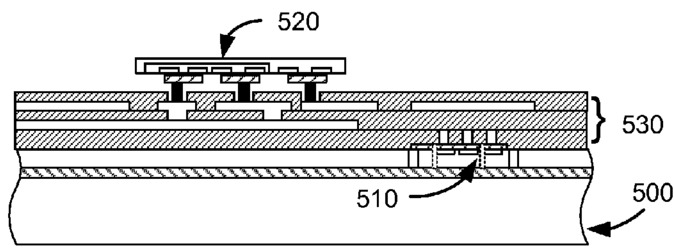
FIG. 5.5
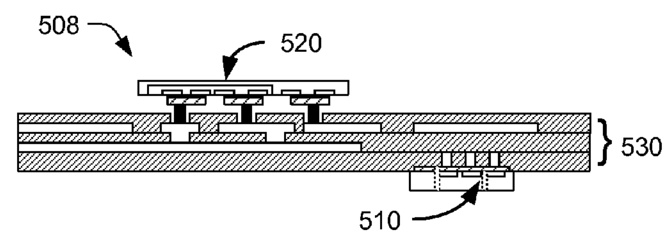

FIG. 6.1
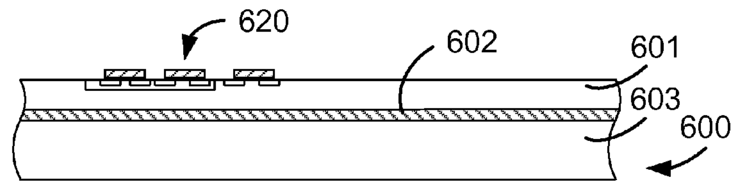
FIG. 6.2
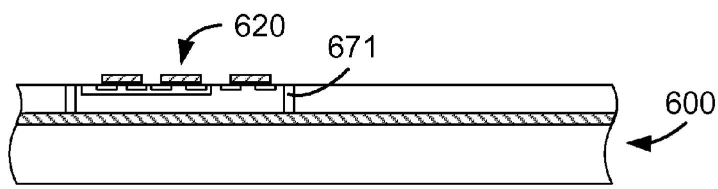
FIG. 6.3
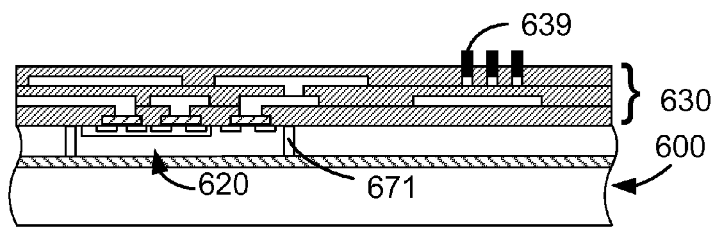
FIG. 6.4
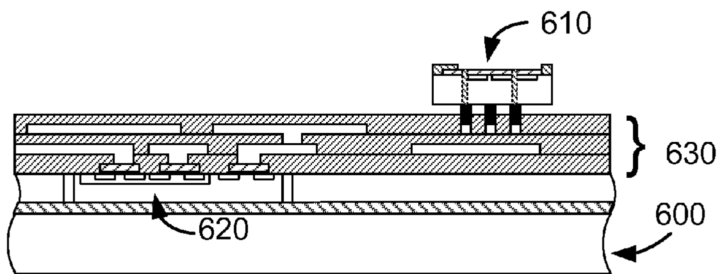
FIG. 6.5
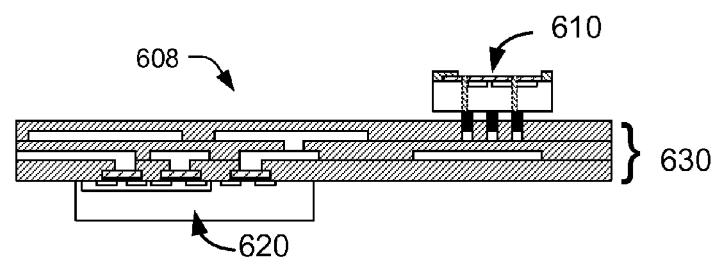

FIG. 7.1
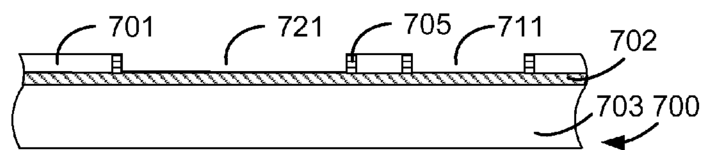
FIG. 7.2
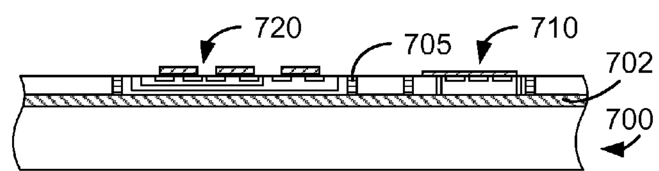
FIG. 7.3
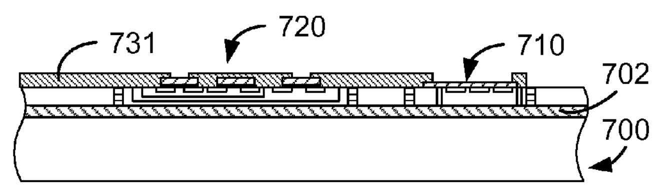
FIG. 7.4
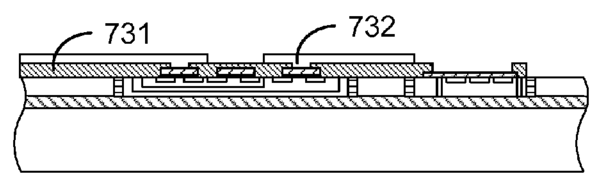
FIG. 7.5
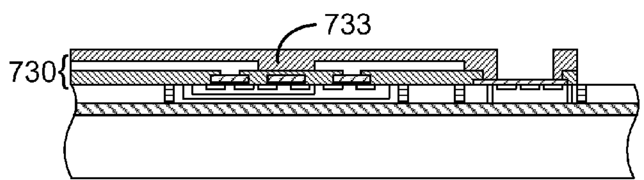
FIG. 7.6
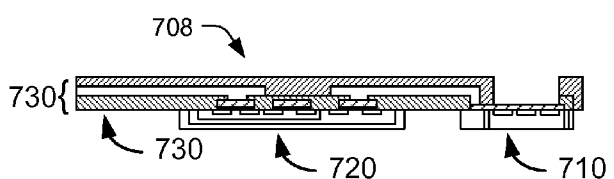

FIG. 8 .1
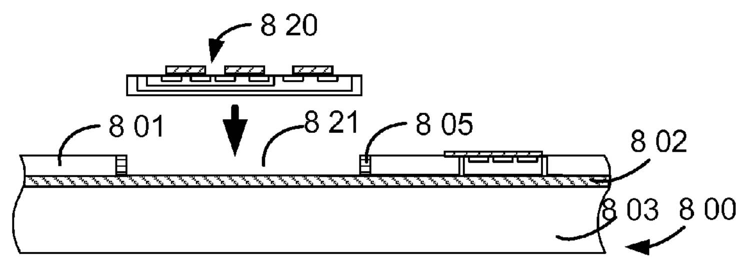
FIG. 8 .2
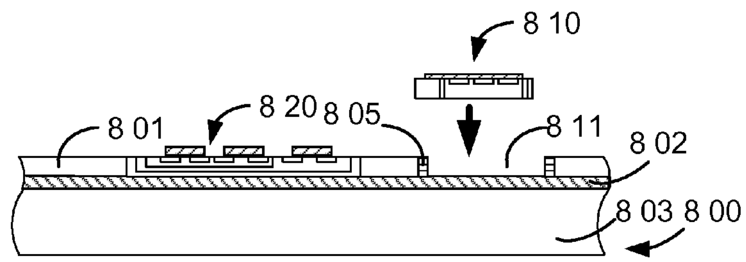

FIG. 10.1
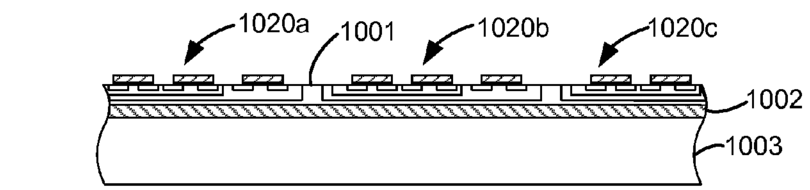
FIG. 10.2
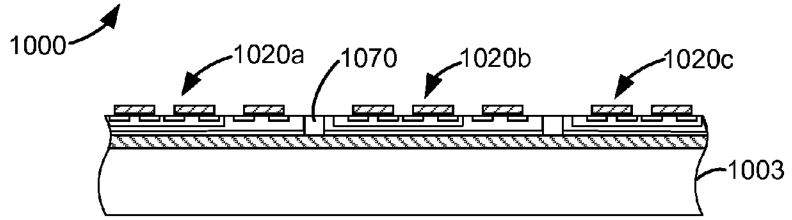
FIG. 10.3
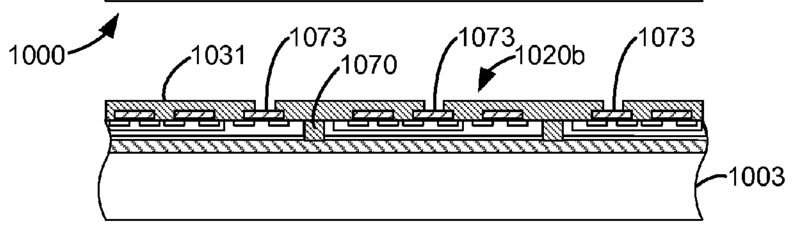
FIG. 10.4
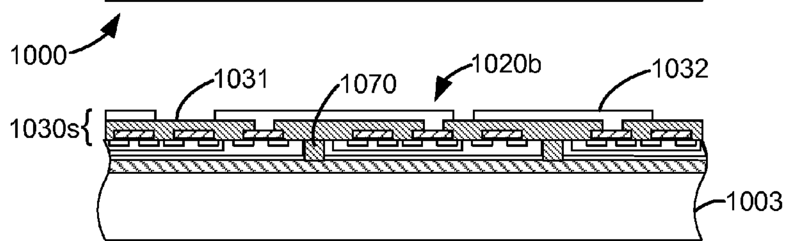
FIG. 10.5
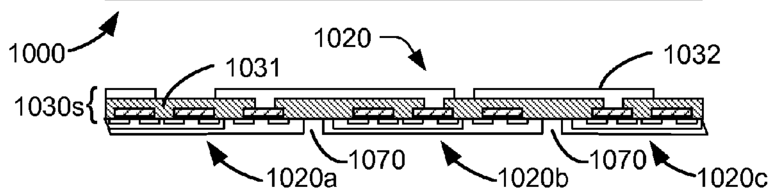

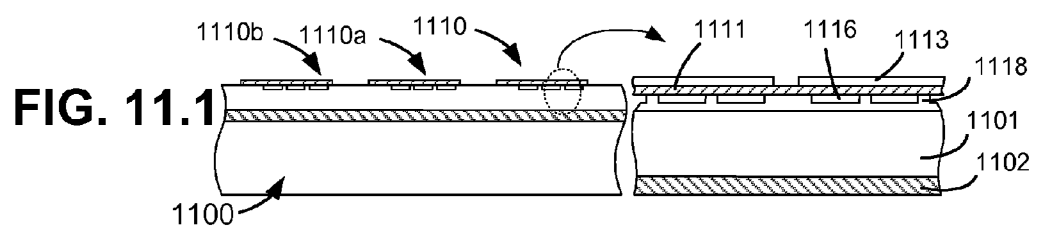
FIG. 11.1
1110b
1110a
1110
1111
1116
1113
1118
1101
1102
1100
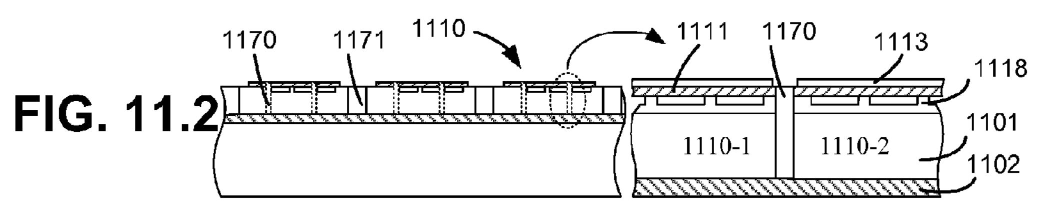
FIG. 11.2
1170
1171
1110
1111
1170
1113
1118
1101
1110-1
1110-2
1102
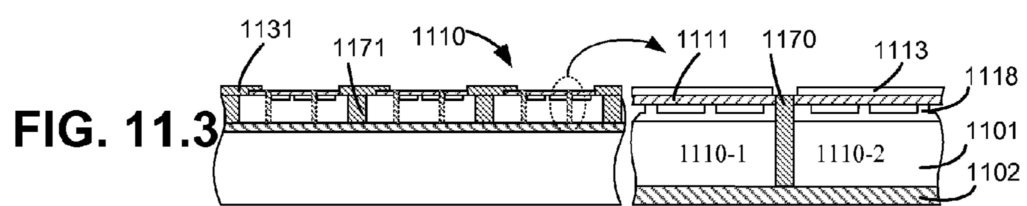
FIG. 11.3
1131
1171
1110
1111
1170
1113
1118
1101
1110-1
1110-2
1102
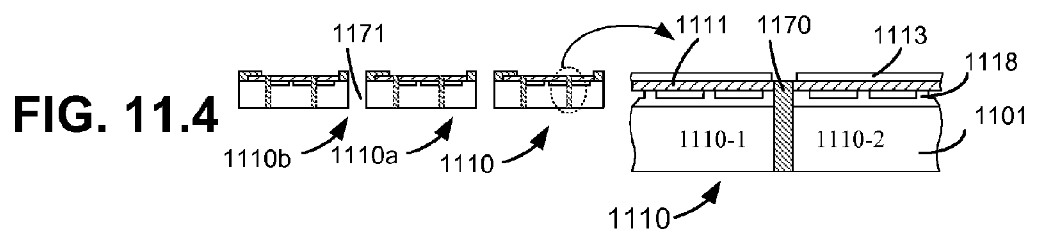
FIG. 11.4
1171
1111
1170
1113
1118
1101
1110-1
1110-2
1110b
1110a
1110
1110

1210
1270
1271
1210
1212
1270
1213
1218
1210-1
1210-2
1200
1221

1210
1270
1271
1210
1212
1270
1213
1218
1210-1
1210-2
1203
1208
1200
1221
1208
1208
1208

1210b
1210a
1210
1210
1212
1216
1213
1218
1271
1270
1210-1
1210-2
1200
1221
1270

CMUT PACKAGING FOR ULTRASOUND SYSTEM

PRIORITY

This application claims priority from U.S. Provisional Application Ser. No. 60/992,020, filed Dec. 3, 2007 and U.S. Provisional Application Ser. No. 61/024,843, filed Jan. 30, 2008.

BACKGROUND

The present application relates to capacitive micromachined ultrasonic transducers (CMUT) and, more particularly to the packaging of CMUT based ultrasonic transducers, devices, and systems A catheter allows surgical personnel to diagnose and treat conditions deep within a patient's body by navigating the distal end of the catheter to the site where some condition might exist. Then, surgical personnel can operate various sensors, instruments, etc. at the site to perform certain procedures with minimal intrusive effect on the patient. One type of device that has found widespread use is the ultrasonic scanner. Ultrasonic scanners generate acoustic waves at frequencies selected for their ability to allow the acoustic waves to penetrate various tissues and other biological structures and return echoes there from. Often, it is desired to select frequencies on the order of 20 MHz or higher. Images of the tissue surrounding the ultrasonic scanner can be derived from these returned echoes. Another type of ultrasonic device is used to perform High-Intensity Focused Ultrasound (HIFU) through an ultrasonic transducer equipped catheter; it can safely and effectively ablate atrial fibrillation (AF) from the outside surface of a beating heart. Two types of ultrasonic transducers exist, those which are based on piezoelectric crystals (i.e., a crystal fabricated from a piezoelectric material or a piezoelectric composite material) and those based on capacitive micromachined ultrasonic transducers (CMUTs and embedded spring CMUTS or ESCMUTs).

CMUTs typically include two spaced apart electrodes with a membrane attached to one of the two electrodes. In operation, an alternating current (AC) signal is used to charge the electrodes to differing voltages. The differential voltage induces movement of the electrode attached to the membrane and hence, the membrane itself. A piezoelectric transducer (PZTs) also applies an AC signal to the crystal therein causing it to vibrate and produce acoustic waves. The echoes returned to the crystal are used to derive images of the surrounding tissue.

Thus, surgical personnel have found it useful to employ ultrasonic scanner equipped catheters to obtain images of certain tissues (e.g. blood vessels), structures, etc. within human (and animal) patients and to view the effects of therapy thereon. For instance, ultrasonic transducers can provide images which allow medical personnel to determine whether blood is flowing through a particular blood vessel.

Some catheters include a single ultrasonic transducer situated at, or near, the distal end of the catheter whereas other catheters include arrays of ultrasonic transducers at the distal end of the catheter. These ultrasonic transducer transducers can be arrange along the side of the catheter and can point outward there from. If so they can be referred to as "side looking" transducers. When the catheter only has one side looking transducer the catheter can be rotated to obtain images of the tissue in all directions around the catheter. Otherwise, the catheter can have ultrasonic transducers pointed in all directions around the catheter.

In other situations, catheters can have ultrasonic transducers arranged at the distal end of the catheter which point in a distal direction from the end of the catheter. These types of ultrasonic transducers can be referred to as "forward looking" transducers. Forward looking transducers can be useful for obtaining images of tissue in front of (i.e. "forward" of) the catheter.

Since in both ultrasound imaging and ultrasound therapy, the ultrasound system focuses ultrasound in a target zone to achieve either imaging or therapy, a catheter based ultrasound system used for imaging can also be configured to perform therapy by selecting a proper ultrasound frequency and energy input.

SUMMARY

Embodiments provide ultrasonic transducers, device, and systems, (e.g. scanners or HIFU devices) and methods of manufacturing ultrasonic systems. More particularly, a method practiced according to one embodiment includes integrating a flexible electronic device (e.g. an integrated circuit) with a flexible member and integrating a flexible ultrasonic transducer (e.g. a portion of a circular CMUT array) with the flexible member. The integrated flexible electronic device, flexible ultrasonic transducer, and flexible member can form a flexible subassembly which is rolled up to form the ultrasonic transducer. The packaging methods disclosed herein can be used to make miniaturized ultrasonic transducers, devices, and systems. These methods can also be used to make flexible ultrasonic transducers, devices, and systems. Moreover, the resulting ultrasonic transducers, devices, and systems can be mechanically flexible. In some embodiments, these ultrasonic transducers, devices, and systems can also be operationally flexible in that they can be applied to a variety of situations including: IVUS/ICE) imaging and various forms of therapy. For example, these ultrasonic transducers, devices, and systems can be used for, but not limited to, high intensity focused ultrasound (HIFU) ablation for AF on a human patient's heart.

In some embodiments, the integration of the flexible electronic device and the flexible ultrasonic transducer with the flexible member occurs at the same time. Furthermore, the integration of the ultrasonic transducer can be performed from the side of ultrasonic transducer which includes its active surface. In the alternative, the integration of the flexible electronic device can occur before (or after) the integration of the flexible ultrasonic transducer. Moreover, the integration of the flexible ultrasonic transducer can include using a semiconductor technique. In some embodiments, the rolled up flexible subassembly forms a lumen which can be coupled to the lumen of a catheter. However, the rolled up flexible subassembly can be attached to a lumen of a catheter instead. In some embodiments, the method includes folding a portion of the flexible member (which hosts the flexible ultrasonic transducer) through an angle of about ninety degrees to form a forward looking ultrasonic transducer. The flexible member of some embodiments can include a pair of arms attached to portions of a circular array of CMUT transducers. As the arms (and the rest of the flexible member) are rolled up, the circular CMUT array can be folded through about ninety degrees to form a ring shaped CMUT array. The ring shaped CMUT array can then be used as a forward looking CMUT array.

One embodiment of an ultrasonic system disclosed herein includes a flexible electronic device (e.g. an integrated circuit), a flexible ultrasonic transducer; and a flexible member with the flexible electronic device and the flexible ultrasonic transducer integrated with the flexible member. The integrated flexible electronic device, the flexible ultrasonic transducer, and the flexible member can form a flexible subassembly which is rolled up to form the ultrasonic scanner. In some embodiments, the rolled up flexible subassembly is a lumen or, instead, can be attached to a lumen of a catheter. The flexible ultrasonic transducer can include a through wafer interconnect and a portion of a circular CMUT array in communication therewith. Moreover, the ultrasonic transducer can be a forward looking, ring shaped CMUT array.

Accordingly, embodiments provide many advantages over previously available ultrasonic transducers and, more particularly, over PZT based ultrasonic systems. For instance, embodiments provide ultrasonic scanners which can operate at higher frequencies and with wider bandwidths than heretofore possible. Embodiments also provide ultrasonic systems with smaller form factors than those of previously available ultrasonic transducers. In addition, embodiments provide methods of manufacturing ultrasonic scanners which are simpler, less costly, and faster than previously available ultrasonic manufacturing methods.

BRIEF DESCRIPTION OF THE FIGURES

FIG. 4 illustrates a method of integrating ICs and CMUT arrays with flexible members for a CMUT based ultrasonic scanner of one embodiment.

FIG. 5 illustrates another method of integrating ICs and CMUT arrays with flexible members for a CMUT based ultrasonic system of one embodiment.

FIG. 6 illustrates another method of integrating ICs and CMUT arrays with flexible members for a CMUT based ultrasonic system of one embodiment.

FIG. 7 illustrates another method of integrating ICs and CMUT arrays with flexible members for a CMUT based ultrasonic scanner of one embodiment.

FIG. 8 illustrates yet another method of integrating ICs and CMUT arrays with flexible members for a CMUT based ultrasonic scanner of one embodiment.

FIG. 10 illustrates a method of manufacturing a flexible IC subassembly for a CMUT based ultrasonic scanner of one embodiment.

FIG. 11 illustrates another method of manufacturing CMUT arrays and CMUT elements for a CMUT based ultrasonic scanner of one embodiment.

DETAILED DESCRIPTION

Figures 1A, 1B:
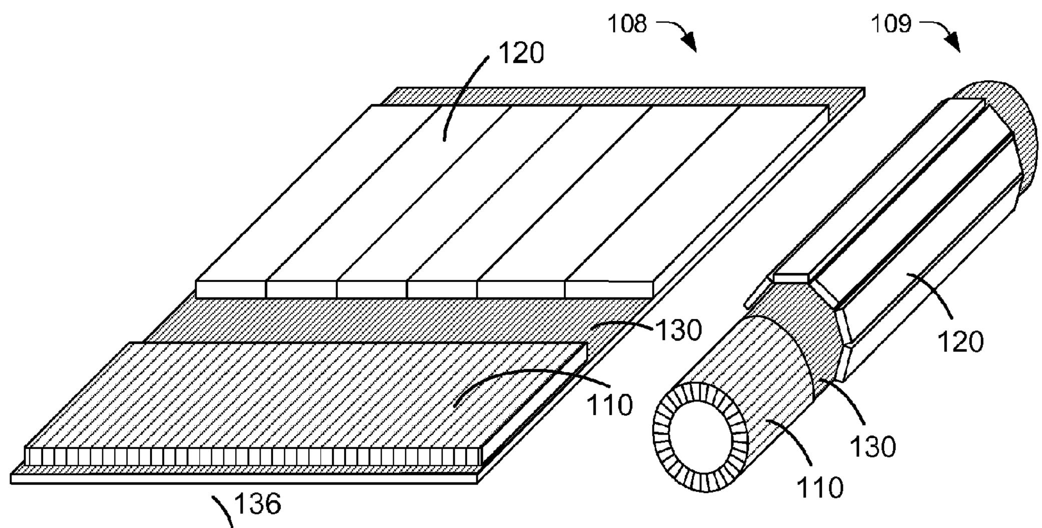
FIG. 1 illustrates a perspective view of a CMUT based ultrasonic scanner and of a flexible subassembly for a CMUT based ultrasonic scanner of one embodiment.

One component of a capacitive micromachined ultrasonic transducer (CMUT) based system (e.g. IVUS/ICE scanner, miniature high intensity focus ultrasound (HIFU) device, etc.) of various embodiments is a flexible member with a CMUT array(s) and/or an IC(s) integrated thereon. The integration of the CMUT arrays and ICs can be performed at the same time using semiconductor and MEMS fabrication and packaging techniques (hereinafter "semiconductor" techniques) or can be performed at different times. Semiconductor techniques can be used in batch processes thereby providing relatively simple, reliable, and cost efficient methods of manufacturing CMUT based ultrasonic systems. The integrated flexible members (with the CMUT arrays and/or ICs) can be folded, or otherwise arranged, to fit within limited spaces and can be made to conform to various surfaces (even those with compound curvature). More specifically, the ultrasonic systems disclosed herein can be included on, or in, various types of catheters. More particularly, these batch semiconductor processes can provide methods of manufacturing ultrasonic systems which are simpler, more reliable, and more cost efficient than methods of manufacturing piezoelectric transducer (PZT) based ultrasonic systems.

Though piezoelectric transducers (PZTs) can perform some desirable diagnostic and therapeutic functions, it remains difficult to obtain piezoelectric transducers (PZTs) with small form factors. More specifically, due to constraints associated with the materials from which PZTs are manufactured, it remains difficult to design and manufacture catheters with PZTs small enough to fit within many catheters designed to be navigated through various cardiovascular vessels, neurovascular vessels, and other biologic structures. Moreover, PZT materials do not lend themselves well to relatively high frequency regimes. For example, it is difficult to design and manufacture a PZT capable of operation in the region near (and above) 20 MHz which is useful for imaging biological tissues.

Furthermore, to form cylindrical arrays of PZT (such as the cylindrical arrays desirable for inclusion on various catheters) the individual PZTs must be diced from flat sheets of the transducers. The individual PZTs can then be arranged in a cylindrical array on the catheter. As a result, some of the individual PZTs (or groups thereof) can be damaged or contaminated with kerf or other contaminants during the dicing and assembly operations. Additionally, the dicing operation and the assembly of the individual PZTs on to the catheter can lead to variations in the operational characteristics of the individual PZTs. Thus, previously available PZTs have found use in only certain ultrasound applications. This disclosure provides CMUT based ultrasonic systems, and catheters equipped with such CMUTs which address at least some of the shortcomings of PZTs. As discussed herein, the CMUT based ultrasonic systems and catheters disclosed herein also possess other advantages.

CMUTs transmit and detect acoustic waves in adjacent media using two plate-like structures arranged to form a capacitor. The plates (or electrodes coupled to the plates) can be repetitively charged to displace one plate relative to the other thereby generating the acoustic waves. Typically, an alternating current (AC) charges the plates. In the alternative, the plates may be charged to a selected voltage (with, for example, a direct current or DC signal) and can be used to sense acoustic waves which impinge on the exposed plate and therefore displace that plate relative to the other plate. The displacement of the exposed plate causes a change in the capacitance of the CMUT. The resulting electric signal generated by the CMUT can be analyzed to generate images of the media surrounding the CMUT. Some CMUT based ultrasonic systems include switches so that, when the switch is in one position, the switch allows the CMUT to transmit acoustic waves and, when the switch is in the other position, the switch allows the CMUT to detect acoustic waves.

CMUTs can be fabricated separately or can be fabricated in various types of arrays. For instance, a one dimensional (1-D) array of CMUTs can be fabricated wherein the various CMUTs are formed in a linear array. 2-D CMUT arrays can also be fabricated in which the various CMUTs are formed in various patterns including, for example, rows and columns. The rows and columns can create arrays which are generally square, rectangular, or other shapes. Moreover, individual CMUTs can be operated separately; can be operated in conjunction with other CMUTs; or can be operated in conjunction with all of the CMUTs in a particular array or scanner. For instance, the signals driving the various CMUTs can be timed to operate a number of the CMUTs as a phased array to direct the acoustic energy in a particular direction(s).

CMUT arrays can be formed to be flexible so that the array can conform to a surface, cavity, etc. with a desired or given shape or curvature. For instance, CMUT arrays can be fitted to conform to the shape of a particular instrument, catheter, or other device. Similarly, the ICs (or other electronic circuits) used to drive the CMUTs (and sense the signals there from) can be formed to be flexible also. Furthermore, the CMUTs and ICs can be integrated with each other and the instrument at the same time using the same techniques or at separate times using the same (or different) techniques as disclosed herein.

More particularly, the CMUTs and ICs of some embodiments can be integrated with each other on a flexible member at the same time using semiconductor or micro electromechanical systems (MEMS) fabrication and packaging techniques (hereinafter "semiconductor" techniques). The flexible member, with the CMUTs and/or ICs on it, can be wrapped onto a catheter (or other device) to form a catheter with a CMUT based ultrasonic system. These CMUT based ultrasonic systems serving as ultrasound scanners can be forward looking, side looking, or combinations thereof. They can also be used to perform imaging, therapeutic functions (e.g. tissue ablation), or combinations thereof. In some embodiments, other transducers (e.g., pressure, temperature, etc.) can be fabricated and integrated with the CMUTs and ICs on the flexible membrane.

FIG. 1A illustrates a perspective view of a flexible subassembly for a capacitive micromachined transducer (CMUT) based ultrasonic system of one embodiment. The flexible subassembly 108 includes a CMUT array 110, support electronics 120 for the CMUT array 110, and a flexible member 130. In some embodiments, the support electronics 120 are in the form of one or more integrated circuits (ICs). The flexible member 130 mechanically couples the CMUT array 110 and the support electronics 120 while allowing the CMUT array 110 and the support electronics 120 to move relative to each other during assembly. Flexible member 130 can also provide electrical connectivity between the CMUT array 110 and support electronics 120. Moreover, each of the CMUT elements with in the CMUT array 110 are flexibly coupled to each other. Likewise, various portions of the support electronics 120 can be flexibly coupled to each other.

FIG. 1B illustrates a perspective view of a CMUT based ultrasonic system (e.g. scanner) of one embodiment. More particularly, the CMUT based ultrasonic system 109 can be formed from the flexible subassembly 108. In one embodiment, flexible subassembly 108 is rolled into a cylindrical shape as indicated by reference arrow 136 to form CMUT based ultrasonic system 109. As illustrated in FIG. 1B, CMUT based ultrasonic system 109 can be a side looking ultrasonic scanner. CMUT based ultrasonic scanner 109 can be attached to a lumen of a catheter, or other device, and can be used to image tissues within a patient's body. CMUT based ultrasonic scanner 109 can also focus the ultrasound into the region generally adjacent to the scanner to do HIFU ablation. While the flexible subassembly 108 can be wrapped around objects, rolled into a tube, partial lumen, or lumen, or formed into other shapes (even those with compound curves).

Figures 2A, 2B:
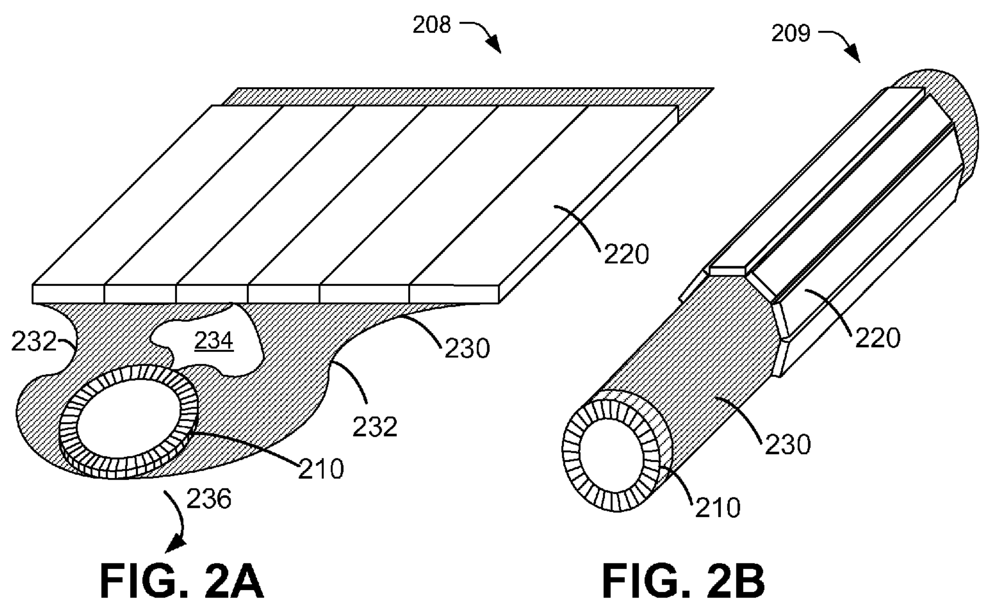
FIG. 2 illustrates a perspective view of another CMUT based ultrasonic scanner and of a flexible subassembly for a CMUT based ultrasonic scanner of one embodiment.

FIG. 2 illustrates a perspective view of another flexible subassembly for a CMUT based ultrasonic system of one embodiment. The flexible subassembly 208 includes a circular CMUT array 210, supporting ICs 220, and a flexible member 230. The flexible member 230 includes a pair of arcuate arms 232, which project from the ICs 220 and to the circular CMUT array 210. The arms 232 can also define a void 234 which will allow arms 232 to conform to the overall cylindrical shape of the CMUT based ultrasonic system 209 illustrated in FIG. 2B. To form the ultrasonic system 209 from the flexible subassembly 208, the circular CMUT array 210 can be folded inward, as indicated at 236, as the flexible subassembly 208 is rolled into a cylindrical shape. Thus, the individual elements of the circular CMUT array 210 can point distally from the CMUT based ultrasonic system 209. Accordingly, the CMUT based ultrasonic system 209 can be a forward looking, CMUT based, ultrasonic scanner. CMUT based ultrasonic scanner 209 can also focus the ultrasound into the region forward of the scanner to do HIFU ablation.

Figures 3A, 3B:
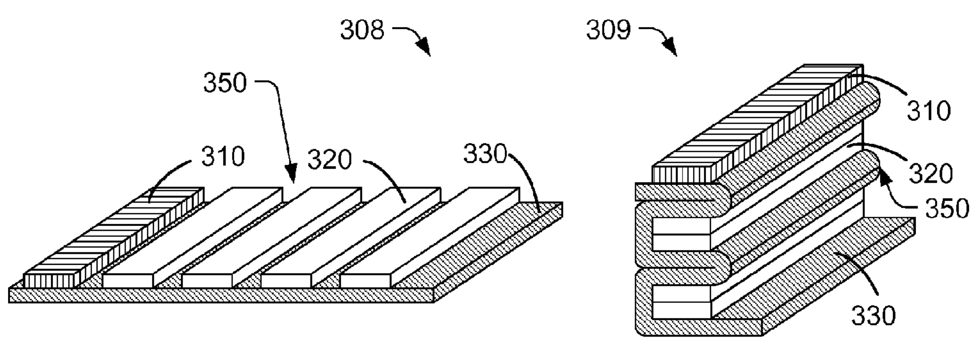
FIG. 3 illustrates perspective views of a flexible subassembly for a CMUT based ultrasonic scanner of one embodiment.

With reference now to FIG. 3A, a perspective view of a flexible subassembly for a CMUT based ultrasonic system of one embodiment is illustrated. The flexible subassembly 308 includes a CMUT array 310 and ICs 320 lying parallel to, and spaced apart from, each other on a flexible member 330. The CMUT array 310 can be a single element CMUT or a CMUT array (e.g. 1 dimensional, 2 dimensional, 1.5 dimensional, or any other types of CMUT arrays). Thus, portions 350 of the flexible member 330 span the distance between at least some of the ICs 320 and the CMUT array 310. The flexible assembly 308 can be folded at these portions 350 of the flexible member 330 to form a compact ultrasonic system 309 (see FIG. 3B). The compact ultrasonic system 309 can resemble a stack of ICs 320 with the CMUT array 310 at one end of the stack and the portions 350 of the flexible member defining layers of the flexible member between the CMUT array 310 and the ICs 320. Compact ultrasonic system 309 can be made small enough so that it can fit within a catheter and within other similarly limited spaces. While the flexible assembly 308 can be folded into a stack, it can also be wrapped around objects, rolled into a tube or lumen, or formed into other shapes (even those with compound curves).

With reference now to FIGS. 4-8, various methods of integrating ICs and CMUT arrays with flexible members are illustrated. These methods can use various semiconductor techniques to perform the integration of the ICs and the CMUT arrays with the flexible members. Indeed, in some embodiments, the same semiconductor techniques are used to integrate the ICs and to integrate the CMUT arrays with the flexible member. In contrast, PZT based ultrasonic scanners require different techniques to integrate the PCT transducers and ICs (or other supporting electronics) of PZT based ultrasonic systems.

FIG. 4 illustrates a method of integrating ICs and CMUT arrays with flexible members to form a flexible subassembly 408 for CMUT based ultrasonic systems of one embodiment. More particularly, the flexible member 430 can be fabricated on the wafer 400 (or some other substrate) using various semiconductor techniques. FIG. 4 further illustrates that a wafer 400 can be used to integrated CMUT arrays 410 and ICs 420 with a flexible member 430. During the integration of the CMUT arrays 410 and the ICs 420, various structures such as a flexible member 430, comprising at least one insulation layer 431-435, at least one conductive layer 432-434, and bonding pads 439, can be formed. In the method illustrated by FIG. 4, the CMUT arrays 410 and the ICs 420 can be fabricated separately.

Due, in part, to the semiconductor techniques used to fabricate the flexible member 430, the dimensions of various interconnects to be formed in the flexible member 430 can be controlled to a greater degree than the corresponding dimensions of interconnects in the printed circuit boards (PCBs) used in PZT based ultrasonic systems. Additionally, the method illustrated by FIG. 4 allows interconnect density to be increased (as compared to PZT based ultrasonic transducer interconnect density) by fabricating multiple conductive layers 432-434 with better dimension control. Thus, miniature ultrasonic systems can be manufactured in accordance with various embodiments.

With reference now to FIG. 4.1, the insulation layer 431 can be coated and patterned on to the wafer 400 to form a first layer of the flexible member 430. Note that the wafer 400 can be a silicon wafer, a glass wafer, or some other substrate and that the insulation layer 431 can be coated or formed, e.g. oxide, nitride, Parylene, polyimide, polymer, PDMS, Kapton, etc.

One of the conductive layers 432 can be formed and patterned on to the wafer 400 (as illustrated by FIG. 4.2) to form various interconnects within the flexible member 430. As noted previously, additional insulation layers 433-435 and additional conductive layers 432-434 can be coated and patterned on to the wafer 400 as desired to form additional interconnects within the flexible member 430 (see FIG. 4.3). The material of the conductive layers 432-434 can be Al, Au, Cr, Ti, Cu, etc.

FIG. 4.4 illustrates that bonding pads 439 can be fabricated and patterned from a conductive material on various interconnects previously to mate with corresponding contacts on the CMUT arrays 410, the ICs 420, and other components. The material from which the bonding pads 439 can be formed and can be selected based on the techniques which, in the process illustrated in FIGS. 4.4 and 4.5, are selected to integrate the CMUT arrays 410 and ICs 420 with the flexible member 430. Thus, as illustrated by FIG. 4.5 the CMUT arrays 410 and the ICs 420 can be positioned on the bonding pads 439 and bonded therewith. More specifically, the bonding, either in device level or wafer level, of the CMUT arrays 410 and the ICs 420 with the bonding pads 439 can be performed with eutectic bonding, thermal compression bonding, as well as various flip-chip bonding methods. The flexible subassembly 408, including the flexible member, 430, the CMUT arrays 410 and the ICs 420, can then be separated from the wafer 400 as illustrated by FIG. 4.6. The flexible member comprises the layers 431-435 and bond pads 439. In some embodiments, the integrated flexible subassembly can then subsequently be assembled into an ultrasonic system. Thus, the CMUT arrays 410 can be integrated with the flexible member 430 using the same techniques as are used to integrate the ICs 420 with the flexible member 430 (and, more particularly, semiconductor batch-process techniques).

FIG. 5 illustrates another method of integrating ICs and CMUT arrays with flexible members for a CMUT based ultrasonic system of one embodiment. More particularly, in stead of forming a flexible member on a prime wafer as shown in FIG. 4, the flexible member 530 in FIG. 5 is formed on a SOI wafer with fabricated CMUT arrays 510.

With reference now to FIG. 5.1, CMUT arrays 510 are fabricated on a SOI wafer 500. The SOI wafer comprises a device layer 501, an insulation layer 502 and a handling layer 503. In FIG. 5.2, a first pattern (e.g., trenches or openings) 570, 571 is formed from a top side of the CMUT fabrication substrate. The first pattern includes trenches (or openings) 571 which may define a boundary of each CMUT array 510 on the wafer and trenches (or openings) 570 which may define a boundary of each CMUT element in a CMUT array 510. The trench's deepest end can reach the insulation layer 502. The first pattern (e.g., trenches or openings) 570, 571 may be done during or after CMUT fabrication. After this step, the subsequent processing can be similar to the method of FIG. 4 from FIG. 4.1 to FIG. 4.4 to form the flexible member 530 on the CMUT array (FIG. 5.3). As illustrated by FIG. 5.4, the ICs 520 can be positioned on the bonding pads 539 and bonded therewith. More specifically, the bonding, either in device level or wafer level, of the ICs 520 with the bonding pads 539 can be performed with eutectic bonding, thermal compression bonding, as well as various flip-chip bonding methods. The handling layer 503 of the SOI wafer 500 may be removed. And then the flexible subassembly 508, including the flexible member 530, the CMUT arrays 510 and the ICs 520, can then be separated from the wafer 500 as illustrated by FIG. 5.5. Furthermore, as illustrated by FIG. 5.5, the method illustrated by FIG. 5 can result in the CMUT arrays 510 being positioned on one side of the flexible member 530 (e.g., the side which was fabricated onto the wafer 500) and the ICs 520 being positioned on the other side of the flexible member 530.

FIG. 6 illustrates another method of integrating ICs and CMUT arrays with flexible members for a CMUT based ultrasonic system of one embodiment. More particularly, in stead of forming a flexible member on a prime wafer as shown in FIG. 4, the flexible member 630 in FIG. 6 is formed on a SOI wafer with ICs 610 fabricated thereon.

With reference now to FIG. 6.1, supporting ICs 620 can be fabricated on a SOI wafer 600. The SOI wafer comprises a device layer 601, an insulation layer 602 and a handling layer 603. In FIG. 6.2, a first pattern (e.g., trenches or openings) 671 can be formed from one side (e.g. the top side) of the IC fabrication substrate. The first pattern includes trenches (or openings) 671 which may define a boundary of each IC 610 on the wafer. The trench's deepest end can reach the insulation layer 602. After this step, the subsequent processing can be similar to the method of FIG. 4 from FIG. 4.1 to FIG. 4.4 to form the flexible member 630 on the ICs 620 (FIG. 6.3). As illustrated by FIG. 6.4, the CMUT arrays 610 can be positioned on the bonding pads 639 and bonded therewith. More specifically, the bonding, either in the device level or wafer level, of the CMUT arrays 610 with the bonding pads 639 can be performed with eutectic bonding, thermal compression bonding, as well as various flip-chip bonding methods. The handling layer 603 of the SOI wafer 600 may be removed. And then the flexible subassembly 608, including the flexible member 630, the CMUT arrays 610 and the ICs 620, can then be separated from the wafer 600 as illustrated by FIG. 6.5.

FIG. 7 illustrates another method of integrating ICs and CMUT arrays with flexible members for a CMUT based ultrasonic system of one embodiment. In the method illustrated by FIG. 7, a flexible member 730 can be formed on various CMUT arrays 710 and ICs 720 using various semiconductor techniques. The method of FIG. 7 can be used to increase the interconnect density of the resulting ultrasonic systems (as compared to PZT based ultrasonic systems and conventional PCBs) by increasing the number of conductive layers and decreasing line width and separation of conductive wires in the flexible member 730. Moreover, the method of FIG. 7 can be performed as a batch process thereby taking advantage of the economies of scale associated with batch semiconductor techniques. Thus, many CMUT arrays 710 and ICs 720 can be integrated on various flexible members 730 at the same time.

With reference now to FIG. 7.1, the method illustrated therein can use a wafer 700 to form the flexible member 730 and to integrate the CMUT arrays 710 and the ICs 720 therewith. More particularly, FIG. 7 illustrates that using a SOI wafer 700 can include an embedded insulation layer 702 and a handling layer 703. Furthermore, FIG. 7 illustrates that various structures such as latch structures 705, insulation layers 731 and 732, and conductive layer 732 can be fabricated on the wafer 700.

More particularly, FIG. 7.1 illustrates that the latch structures 705 can be formed on wafer 700. These latch structures can be designed on the wall of the cavities 721 to latch the CMUT arrays 710 and the ICs 720 in place in cavities 721 formed at locations selected for the CMUT arrays 710 and ICs 720. The CMUT arrays 710 and the ICs 720 can be latched in place in their respective cavities 721 using the latch structures 705 (FIG. 7.2). The insulation layer 731 can then be formed and patterned (to provide access to the CMUT arrays 710 and the ICs 720) on the wafer 700 using various semiconductor techniques such as spin-coating, evaporating, sputtering, depositing, etc (FIG. 7.3). Moreover, the insulation layer 731 can be formed from various insulating materials such as Parylene, PMDS, polyimide, polymer, oxide, nitride, etc.

With reference now to FIG. 7.4 a conductive layer 732 can be formed on the wafer 700 to provide various interconnects within the flexible member 730 and between the CMUT arrays 710, the ICs 720, and various other components. The conductive layer 732 can be formed and patterned on the wafer 700 from various conductive materials such as Al, Au, Cu, Ti, etc. Moreover, the conductive layer 732 can be fabricated using various semiconductor techniques such as evaporation, sputtering, depositing, etc. If desired, additional insulation layers 731 and conductive layers 732 can be formed on the wafer 700 to increase the interconnect density of the resulting flexible member 730.

FIG. 7.5 illustrates that the flexible insulation layer 733 can be formed and patterned on the wafer 700 as a protection layer of the flexible subassembly 708. The flexible insulation layer 733 can be formed from various insulating materials such as Parylene, PMDS, polyimide, polymer, oxide, nitride, etc. and can be fabricated via spin-coating, evaporation, sputtering, deposition, etc. The flexible insulation layer 733 can be fabricated with sufficient thickness and material properties to protect the flexible member 730 (and its various layers 731-732 as well as the CMUT arrays 710 and the ICs 720) from mechanical abuse and from the environment.

FIG. 7.6 illustrates that, the handling layer 703 and the insulation layer 702 can be removed from the surface of the wafer 700 which is opposite the side of the wafer 700 which hosts the CMUT arrays 710, the ICs 720, and the flexible member 730. Thus, the flexible subassembly 708 including the integrated flexible member 730, the CMUT arrays 710 and ICs 720, can be removed from the wafer 700. Accordingly, the integrated flexible member 730 can be used to assemble various ultrasonic systems.

FIG. 8 illustrates yet another method of integrating ICs and CMUT arrays with flexible members for a CMUT based ultrasonic scanner of one embodiment. More particularly, FIG. 8.1 illustrates that the CMUT arrays 810 can be fabricated on the wafer 800 first and then the ICs 820 can be latched in place by the latch structures 805 in the wafer with fabricated CMUT arrays. In contrast, FIG. 8.2 illustrates that the ICs 820 can be fabricated on the wafer 800 first and then the CMUT arrays 810 can be latched in place in the wafer with fabricated ICs. In the methods illustrated by FIGS. 8.1 and 8.2, the fabrication of the flexible member 830, and its integration with the CMUT arrays 810 and the ICs 820 can be similar to the method illustrated by FIGS. 7.2-7.6. The finished flexible subassembly can be similar to the flexible subassembly 708 in FIG. 7.6.

Figure 9:
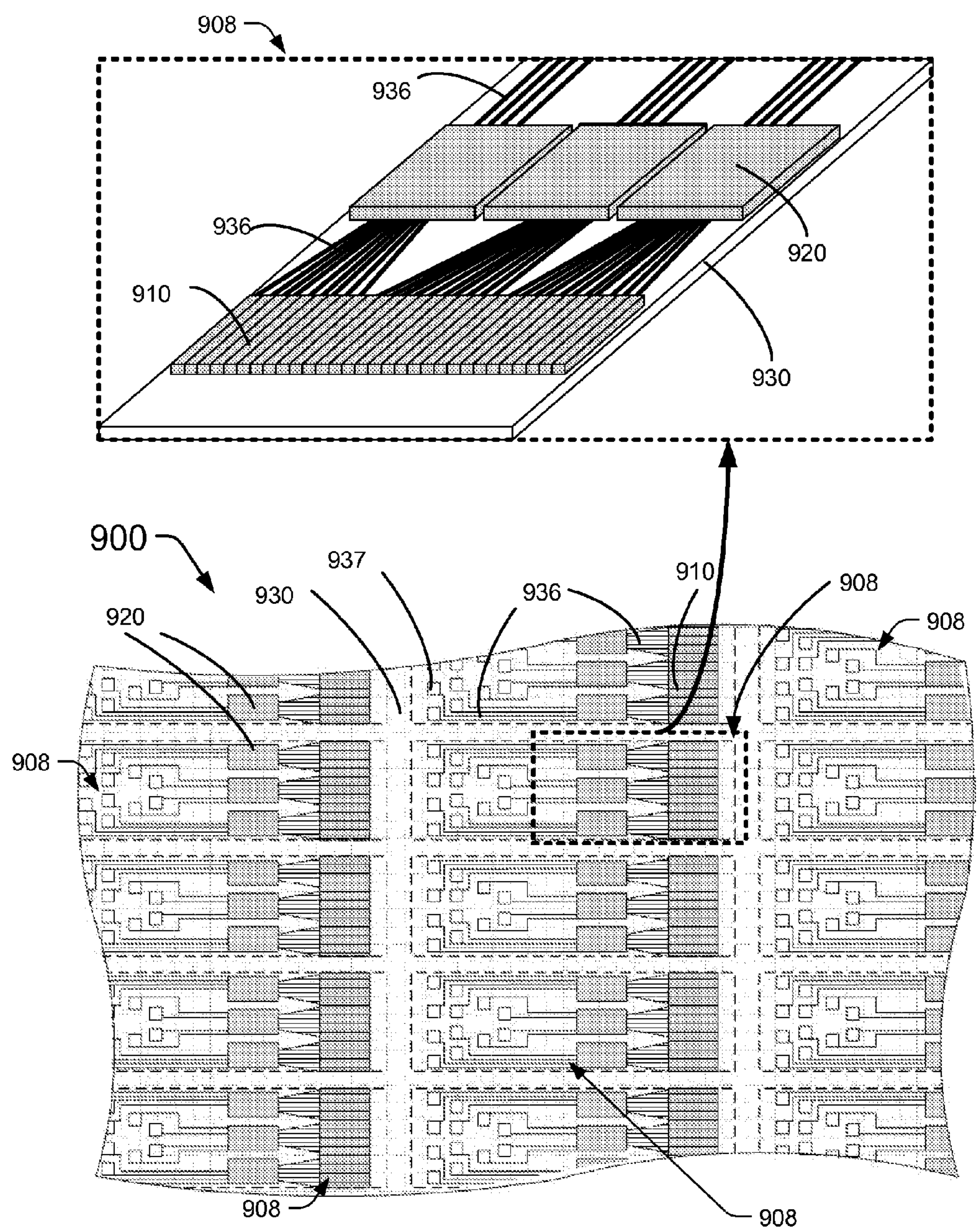
FIG. 9 illustrates perspective views of a flexible subassembly for a CMUT based ultrasonic scanner of one embodiment.

FIG. 9 illustrates a top view of a flexible assembly 900 in which multiple CMUT arrays 910 and multiple ICs 920 packaged on a flexible member 930 to form multiple CMUT based flexible subassemblies 908 of one embodiment. The flexible assembly 900 with multiple flexible subassemblies 908 can be built using the methods illustrates in FIGS. 4-8. Each flexible subassembly 908 can be used to built a CMUT based ultrasound system The CMUT based ultrasonic flexible assembly 900 illustrated by FIG. 9 can be manufactured using methods similar to the methods disclosed herein. More particularly, the figure in the zoomed window in FIG. 9 illustrate a perspective view the CMUT based ultrasonic system built from the flexible subassembly 908 can include a CMUT array 910 and ICs 920 integrated with the flexible member 930 using various batch semiconductor techniques. Moreover, various contact pads 937 in the flexible member 930 can be fabricated to provide an electronic interface with components external to the CMUT based ultrasonic systems 908. Thus, the interconnects 936 (between the CMUT arrays 910, the ICs 920, and various other components) and the contact pads 937 in the flexible member 930 can be fabricated with the dimensional accuracy provided by various semiconductor techniques at the same time.

In the methods described in FIGS. 4-8, at least one of CMUT arrays (e.g. 410, 710) and ICs (e.g. 420, 720) can be separated from a first substrate (e.g. their original fabrication substrate) and then can be integrated on a flexible member (e.g. 430, 730) on a second packaging substrate (e.g. 400, 700). Therefore, at least one of the CMUT arrays and ICs can be fabricated first on their original fabrication substrate and can then be separated and can be ready for the packaged methods described herein. Usually, multiple ICs can be integrated on a flexible member individually. But they can also be integrated with a flexible sub-member on their original fabrication substrate first to form a flexible IC, and then the flexible ICs can be integrated with a CMUT array on the flexible member on the packaging substrate. Usually, CMUT arrays with multiple elements can be made to be flexible before they are integrated with ICs on the flexible member on the packaging substrate. FIGS. 10-12 illustrate several methods to make flexible CMUT arrays (e.g. 410, 720) and flexible ICs (e.g. 410, 720) which can be used in the packaging methods in FIGS. 4-8 as well as other methods.

With reference to FIGS. 10-12, it can be desirable to form through wafer interconnects for multiple elements in the CMUT arrays and multiple chips in the electronics (and other components) of various ultrasonic systems. Moreover, it can be desirable to form the interconnections from the inactive side of the flexible CMUT arrays. Thus, it may be desired to fabricate through wafer interconnects in the CMUT arrays and ICs. Flexible CMUT arrays or ICs which include through wafer interconnections, and methods of fabricating such flexible CMUTs or ICs, are described in International Patent Application No. PCT/IB2006/051566, entitled THROUGH-WAFER INTERCONNECTION, filed on May 18, 2006 by Huang; U.S. patent application Ser. No. 11/425,128, entitled FLEXIBLE MICRO-ELECTRO-MECHANICAL TRANSDUCER, filed on Jun. 19, 2006, by Huang; International Patent Application No. PCT/US2008/085374, entitled THROUGH-WAFER INTERCONNECTIONS IN ELECTROSTATIC TRANSDUCER AND ARRAY, filed on Dec. 3, 2008 by Huang, and International Patent Application No. PCT/US2008/085352, entitled PACKAGING AND CON- NECTING ELECTROSTATIC TRANSDUCER ARRAYS, filed on Dec. 3, 2008 by Huang which are incorporated herein as if set forth in full.

As described in the foregoing patent applications, flexible CMUT arrays or ICs can be formed generally as follows. A pattern of separation trenches can be formed in a wafer hosting ICs, CMUT arrays, or a combination thereof. The trenches can be formed from the side of the wafer hosting the ICs or CMUT arrays. These trenches can be formed to a selected depth and can subsequently be filled with a desired material (for example, an insulator). Material can be removed from the side of the wafer opposite the side hosting the ICs or CMUT arrays until the trenches are exposed. FIGS. 10-12 illustrate various methods of forming flexible CMUTs or ICs of various embodiments.

Now with reference to FIG. 10, many ultrasonic scanners contain more than one IC to support the ultrasonic transducers and, perhaps, perform other functions. In accordance with one embodiment, the multiple ICs can be integrated with the flexible member of an ultrasonic scanner using semiconductor techniques. More particularly, the ICs can be fabricated as flexible ICs and then integrated with the flexible member.

Furthermore, FIG. 10 illustrates that a flexible IC 1020 having a flexible sub-member 1030*s* (see FIG. 10.5) and multiple IC chips 1020*a*-1020*c* can be fabricated from a SOI wafer 1000 on which various structures are fabricated such as: a device layer 1001, an insulation layer 1002, a handling layer 1003, one or more ICs 1020*a*-1020*c*, an insulation layer 1031, a conductive layer 1032, and various trenches 1070. As illustrated by FIG. 10.1, multiple ICs 1020*a*-1020*c* can be fabricated on the SOI wafer 1000 with a thickness which can be defined by the device layer 1001. FIG. 10.2 illustrates that a pattern of trenches 1070 can be etched through the device layer 1001 to reach the insulation layer 1002. In a subsequent step, the back side of the wafer 1000 including the insulation layer 1002 and the handling layer 1003 can be removed to reach the trenches 1070 thereby creating the flexible IC 1020. The insulation layer 1031 can be coated on to the wafer 1000 with a pattern selected to leave various contacts 1073 on the ICs 1020*a*-1020*c* exposed (as illustrated by FIG. 10.3). The insulation layer 1031 may be made of a flexible material such as Parylene, polymer, polyimide, polydimethylsiloxane (PDMS), oxide, nitride, etc. The flexible sub-member 1030*s* comprises one insulation layer 1031 and one conductive layer 1032 in FIG. 10.5. However, the flexible sub-member 1030*s* may comprise multiple insulation layers 1031 and multiple conductive layers 1032 to increase its connection density by repeating the process steps from FIG. 10.3 and FIG. 10.4.

FIG. 10.4 illustrates that the conductive layer 1032 can be coated on to the wafer 1000 in a pattern selected to provide interconnects to the ICs 1020. If desired to (for example) increase the density of the interconnects, additional insulation layers 1031 and conductive layers 1032 can be coated on to the wafer 1000. The handling layer 1003 and insulation layer 1002 can be removed, as illustrated by FIG. 10.5, to expose the trenches 1070. Note that with the trenches 1070 exposed, the only materials connecting the ICs to each other can be the flexible sub-member 1030*s* having the insulation layer 1031 and the conductive layer 1032. Thus, by selecting the dimensions and materials of these layers 1031 and 1032, the flexible sub-member 1030*s* can be fabricated to allow the various IC chips 1020 to move relative to one another during assembly yet still remain interconnected. Thus, the flexible sub-member 1030*s* can be made to be flexible with the layers 1031 and 1032 forming the flexible IC 1020. Subsequently, various CMUTs, CMUT arrays and other devices can be integrated with the flexible IC 1020 in a flexible member using the methods illustrated in FIGS. 4-8 as well as other methods.

With reference now to FIG. 11, another method of manufacturing CMUT arrays with multiple CMUT elements for a CMUT based ultrasonic system of one embodiment is illustrated. The CMUT arrays illustrated by FIG. 11 can be integrated with the flexible member of an ultrasonic system using semiconductor techniques. More particularly, the CMUT arrays can be fabricated as flexible CMUT arrays and then integrated with the flexible member.

Figures at the left side in FIG. 11 show that the multiple CMUT arrays 1110, 1110*a* and 1110*b* are fabricated in the same substrate 1100. Figures at the right side in FIG. 11 are detailed views of portion of the CMUT array 1110 which show the structure of the CMUT elements 1110-1 and 1110-2 in a CMUT array 1110 in more detail.

More specifically, FIG. 11.1 illustrates that flexible CMUT arrays 1110 can be fabricated from a SOI wafer 1100 (including a handling wafer 1103, insulation layer 1102 and the device layer 1101) on which a substrate or bottom electrode 1101, an insulation layer 1102, CMUT arrays 1110 (or CMUT elements), an insulation layer 1131, and various trenches 1170 and 1171 can be fabricated. Each of the CMUT arrays 1110 can include a flexible membrane 1111, a first electrode 1113, a cavity 1116, and a spring anchor 1118 among other possible components. These components 1111, 1113, 1116, and 1118 of the CMUT can be seen in greater detail in the detailed view shown in FIGS. 11.1-11.4. Also, in some embodiments, the CMUTs can be embedded spring ESCMUTs.

FIG. 11.2 illustrates that once the CMUT arrays 1110 have been fabricated, a pattern of trenches 1170 (which separate the CMUT from each other) can be fabricated. These trenches 1170 can be sufficiently deep that they reach the insulation layer 1102 which, as discussed herein, can be removed to expose the trenches. In some embodiments, the trenches 1170 and 1171 are formed during the fabrication of the CMUT arrays 1110. At the same time that trenches 1170 are formed, another pattern of trenches 1171 can be fabricated. These trenches 1171 can be formed so that when the insulation layer 1102 is removed, the trenches 1171 are also exposed thereby separating various CMUT arrays 1110 from each other. The trenches 1170 can define the boundaries of individual CMUT transducer elements 1110-1 and 1110-2. The trenched 1171 can define boundaries of individual CMUT transducer arrays 1110, 1110*a* and 1110*b* on the same wafer.

The insulation layer 1131 can be patterned and coated on the wafer 1100 to leave the active surfaces of the CMUT arrays 1110 exposed as illustrated in FIG. 11.2. As the insulation layer 1131 is fabricated, the material from which it is fabricated may fill the trenches 1170 and 1171. The insulation layer 1131 can be made of various semiconductor materials such as Parylene, polyimide, polymer, PDMS, oxide, nitride, etc.

FIG. 11.4 illustrates that the insulation layer 1102 can be removed to expose the trenches 1170 and 1171 (which can lie between individual CMUT elements and CMUT arrays 1110, respectively). Thus, the CMUT arrays 1110 can have multiple CMUT elements 1110-1 and 1110-2, can be separated from each other as illustrated by FIG. 11.4. These CMUT arrays 1110 and the CMUT elements can subsequently be integrated on various flexible members such as flexible members 130, 230, and 330 (see FIGS. 1-3) using the methods illustrated in FIGS. 4-8. While FIG. 11 illustrates that the wafer 1100, from which the CMUT arrays 1110 can be fabricated, can be a silicon-on-oxide wafer, other types of wafers can be used to fabricate the CMUT arrays 1110. For instance, a prime wafer can be used to fabricate the CMUT arrays 1110 (or the CMUT elements).

Figures 12A, 12B, 12C:
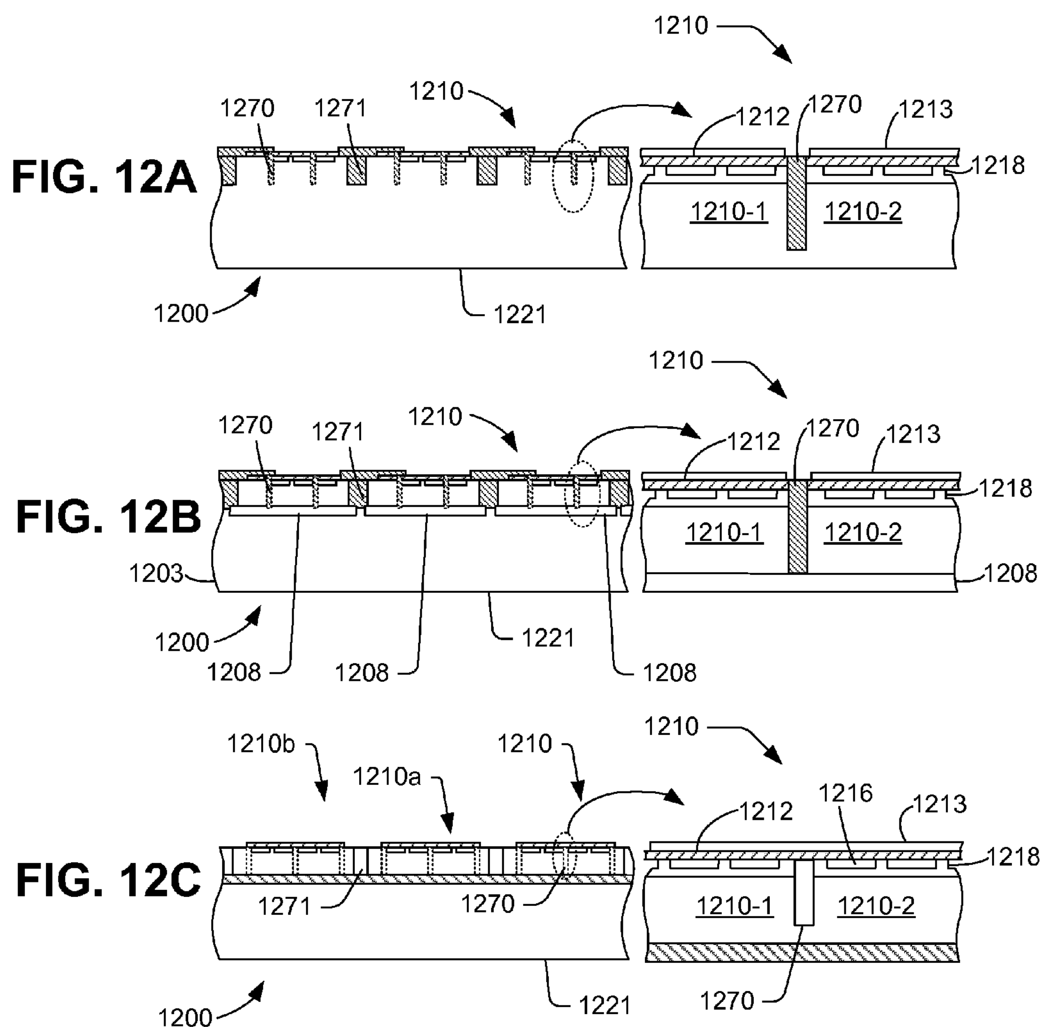
FIG. 12 illustrates methods of various embodiments of manufacturing CMUT arrays.

FIG. 12 illustrates methods of various embodiments of manufacturing CMUT arrays from prime wafers. More specifically, FIG. 12A illustrates that the trenches 1270 and 1271 can be etched (from the side of the wafer hosting the CMUT arrays 1210) to a selected thickness. Then, in some embodiments, the wafer 1200 can be thinned (from the side 1221, which is opposite the CMUT arrays 1210) until the trenches 1270 and 1271 are exposed. Thus, the CMUT arrays 1210 (or CMUT elements) which are hosted on the prime wafer 1200 can be separated from each other.

With reference now to FIG. 12B, another method of manufacturing CMUT arrays 1210 of one embodiment is illustrated. In the method illustrated in FIG. 12B, the method can begin with a wafer 1200, which includes an embedded cavity 1208. The CMUT arrays 1210 can be fabricated on regions of the wafer 1200 adjacent to the cavities 1208. The trenches 1270 and 1271 can then be etched into the wafer 1200 and can reach the embedded cavities 1208. Thereafter, in some embodiments, the wafer 1200 can be thinned (e.g., the handling wafer 1203 can be removed) to expose the trenches 1270 and 1271 thereby separating the CMUT arrays 1210 (and the CMUT elements).

With reference now to FIG. 12C, another method of manufacturing CMUT arrays 1210 of one embodiment is illustrated. Instead of forming the trenches 1270 and 1271 after finishing CMUT fabrication, the trenches 1270 and 1271 can be formed during the CMUT fabrication. For example, the trenches 1270 and 1271 in FIG. 12C can be etched before the formation of the membrane 1212 and top electrode 1213. According to some embodiments, the trenches embedded under the membrane 1212 can avoid etching the top electrode 1213 and the membrane 1212 during the trench etching in the method illustrated in FIG. 11.2. This may be desirable for the implementation of some CMUT systems. After the CMUT arrays with the embedded trenches 1270 and 1271 are fabricated, the process used to form the flexible CMUT arrays 1210 is similar to the process illustrated in FIG. 11, FIG. 12A and FIG. 12B.

CMUT based ultrasonic scanners provide several advantages over PZT based ultrasonic scanners. These advantages arise, in part, from the relatively low acoustic impedance of CMUTs. CMUTs typically have lower acoustic impedances than air, water, tissue, etc. As a result, and unlike PZTs, CMUTs can be used without a layer of material to match the acoustic impedance of the CMUTs with the acoustic impedance of the surrounding media.

PZTs also transmit acoustic energy (i.e., acoustic waves) from both their front and rear surfaces. As a result of this characteristic, PZTs require a backing layer on their rear surface to absorb the acoustic energy emitted there from. Otherwise the acoustic waves transmitted from the rear of the PZTs could reflect from various structures and interfere with the operation of the PZTs. However, in absorbing the acoustic energy transmitted from the rear of the PZTs, the backing layers generate heat. As a result, PZTs can become warm, or even hot, during operation thereby reducing their desirability for use in certain applications such as HIFU. Since CMUTs transmit acoustic energy only from there front surfaces, heating due to misdirected acoustic energy is not a concern for CMUT based ultrasonic scanners. Furthermore, the backing layers (and acoustic matching layers discussed previously) complicate the manufacturing of PZT based ultrasonic systems. In contrast CMUT based ultrasonic systems can omit these layers and the attendant manufacturing steps.

Moreover, CMUT based ultrasonic scanners can be produced using semiconductor manufacturing techniques. Since these semiconductor techniques benefit from decades of investments by various portions of the semiconductor industry, these techniques can provide relatively high levels of uniformity, precision, repeatability, dimensional control, repeatability, etc. in the CMUTs thereby produced. Further still, many of the foregoing semiconductor techniques can be batch processes. As a result, economies of scale associated with these techniques allow for lower per unit costs for CMUT based ultrasonic systems, particularly when relatively large volumes of ultrasonic systems may be desired. For instance, since all of the features of the CMUT arrays on a particular wafer can be patterned simultaneously, the fabrication of multiple CMUT arrays introduce no (or little) overhead as compared to the fabrication of a single CMUT array.

Additionally, since CMUT based ultrasonic systems can be produced with semiconductor techniques, integrated circuits (ICs) and other semiconductor devices can be integrated with the CMUT arrays with relative ease. Thus, the CMUT arrays and the ICs can be fabricated on the same wafer at the same time using the same techniques. In the alternative, CMUTs and ICs can be integrated into various transducers at different times. Furthermore, CMUTs and ICs can be fabricated from the same, or similar, biocompatible materials.

In contrast, the fabrication and integration of PZTs with other components (e.g., ICs) using semiconductor techniques is impracticable due to constraints imposed by the PZT materials Moreover, the available PZT related fabrication and integration techniques suffer from several disadvantages including being labor intensive, being expensive, being subject to manufacturing variations, etc. Furthermore, available PZT techniques meet with additional difficulties as the size of the individual PZT devices approaches the small dimensions (e.g., tens of microns) required for relatively high frequency devices. For instance, separation of the individual PZT devices is dominated by lapping and dicing techniques which lead to device-to-device variability.

Accordingly, CMUT based ultrasonic systems enjoy both performance and cost advantages over PZT based ultrasonic systems. More particularly, since it is typically desirable for ultrasonic systems to have transducers with both high frequency operating ranges and small physical sizes, CMUT based ultrasonic systems can have several advantages over PZT based ultrasonic systems.

First, CMUT based ultrasonic systems can be fabricated with better dimensional control than PZT based ultrasonic systems. More particularly, CMUT based ultrasonic systems can be fabricated with minimum dimensions less than about 1 micrometer whereas the minimum dimensions of PZT based ultrasonic systems are greater than about 10 micrometers. Accordingly, CMUT based ultrasonic systems can be fabricated with correspondingly smaller CMUT element pitches. Secondly, the minimum width and pitch of CMUT based ultrasonic system interconnects can be less than about 2-3 micrometers whereas the minimum interconnect width and pitch for PZT based ultrasonic systems is greater than about 25 micrometers. Thus, CMUT based ultrasonic system interconnects can be fabricated at higher densities than PZT based ultrasonic system interconnects. Accordingly, CMUT based ultrasound systems can possess more transducers (for a given system size) or can be smaller (for a given number of transducers) than PZT based ultrasonic systems.

Moreover, given the improved device size of CMUT based ultrasonic scanners, as compared to PZT based ultrasonic scanners, CMUT based ultrasonic scanners can be created which can operate up to about 100 MHz. In contrast, PZT based ultrasonic scanners are limited to operating regions well below 20 MHz. Furthermore, since the resolution of an ultrasonic transducer depends on its operating frequency, CMUT based ultrasonic scanners can be fabricated with correspondingly improved resolution. For similar reasons, the bandwidth of CMUT based ultrasonic scanners is wider than the bandwidth of PZT based ultrasonic scanners. Accordingly, CMUT based ultrasonic scanners can be applied to more situations than PZT based ultrasonic scanners.

The simpler design and fabrication of CMUT based ultrasonic systems (as compared with PZT based ultrasonic transducers) also gives rise to certain advantages. For instance, since the ICs used to support the CMUTs and the CMUTs themselves can be fabricated with the same techniques, fabrication of the CMUTs and ICs, taken together, can be simplified. Additionally, because CMUTs do not require matching or backing layers, the manufacturing steps associated with these layers can also be eliminated. Likewise, steps associated with integrating the CMUTs and the ICs can be eliminated or, if not, simplified.

The present disclosure is described with reference to specific embodiments thereof, but those skilled in the art will recognize that the present disclosure is not limited thereto. Various features and aspects of the above-described disclosure may be used individually or jointly. Further, the present disclosure can be utilized in any number of environments and applications beyond those described herein without departing from the broader spirit and scope of the specification. We claim all such modifications and variations that fall within the scope and spirit of the present disclosure. The specification and drawings are, accordingly, to be regarded as illustrative rather than restrictive.

What is claimed is:

1. A method of packaging an ultrasonic system, the method comprising:

disposing, on a substrate, a capacitive micromachined ultrasonic transducer (CMUT) and an integrated circuit (IC);

applying an insulation layer of a first material and a conductive layer of a second material to the substrate and at least one of the CMUT or the IC;

removing the substrate to obtain a subassembly comprising:

the insulation layer, the conductive layer, the CMUT, and the IC; and shaping the subassembly to have at least one curved part.

2. The method of claim 1 wherein the first material is a flexible polymer.

3. The method of claim 1 wherein at least one of the CMUT or the IC is disposed on the substrate by being placed into a structure formed on the substrate.

4. The method of claim 1 wherein at least one of the CMUT or the IC is disposed on the substrate by being fabricated on a device layer of the substrate before the applying the insulation layer and the conductive layer.

5. The method of claim 4 further comprising forming a trench in the device layer of the substrate to define a portion of a boundary of at least one of the CMUT or the IC.

6. The method of claim 5 further comprising forming the device layer with at least one embedded cavity.

7. The method of claim 4 further comprising forming the device layer on a SOI wafer, wherein the substrate comprises at least the device layer and the SOI wafer.

8. The method of claim 1, wherein:

the applying the insulation layer comprises applying the insulation layer, at least partially, over the IC and the CMUT to mechanically connect the CMUT and the IC; and the applying the conductive layer comprises applying the conductive layer to electrically connect the CMUT and the IC.

9. The method of claim 1 wherein the disposing comprises fabricating the CMUT on the substrate prior to the applying the insulation layer and the conductive layer, the method further comprising connecting the IC to the conductive layer on a side of the insulation layer opposite to the CMUT.

10. The method of claim 1 wherein the shaping the subassembly further comprises shaping the subassembly to define a lumen or a partial lumen.

11. The method of claim 1 the method further comprising forming a through-wafer interconnect in the CMUT, wherein the at least one conductive layer is on a side of the CMUT that does not include an active surface of the CMUT.

12. The method of claim 1 further comprising attaching the shaped subassembly to a lumen.

13. The method of claim 1 wherein the CMUT includes an array of CMUTs.

14. The method of claim 1, wherein the shaping further comprising folding a portion of the at least one insulation layer and the at least one conductive layer to form a forward looking ultrasonic transducer.

15. The method of claim 1 wherein:

at least prior to the shaping, the CMUT includes at least a portion of a circular CMUT array.

16. The method of claim 1 wherein the insulation layer and the conductive layer make up at least a portion of a flexible member, such that one of the IC or the CMUT is integrated on a first side of the flexible member, the method further comprising integrating the other one of the IC or the CMUT on an opposite side of the flexible member.

17. An ultrasonic system comprising:

a plurality of electronic integrated circuits (ICs);

an ultrasonic transducer; and a flexible member extending between and integrated with the ICs and the ultrasonic transducer, the flexible member including at least one insulation layer and at least one conductive layer, wherein the flexible member is shaped into a folded configuration so that at least one of the ICs is stacked over another one of the ICs, the ultrasonic transducer is stacked over the stacked ICs, and at least a portion of the flexible member defines a layer between the ultrasonic transducer and the stacked ICs.

18. The system of claim 17 wherein the flexible member includes at least one layer of a flexible polymer.

19. The system of claim 17 wherein the flexible member includes:

a first flexible insulation layer, a flexible patterned conductive layer including a plurality of interconnects between the ICs and the ultrasonic transducer, and a second flexible insulation layer, such that at least a portion of the conductive layer is between the first flexible insulation layer and the second flexible insulation layer.

20. The system of claim 17 wherein the ultrasonic transducer includes a through-wafer interconnect.

21. The system of claim 17 wherein the ultrasonic transducer includes at least one capacitive micromachined ultrasonic transducer element.

22. The system of claim 17 wherein the ultrasonic transducer is a capacitive micromachined ultrasonic transducer (CMUT) array including at least two CMUT elements.

23. The system of claim 17 further comprising at least one of a temperature sensor or pressure sensor integrated with the flexible member.

24. The system of claim 17 wherein the ultrasonic transducer includes at least a portion of a circular capacitive micromachined ultrasonic transducer array that is circular at least prior to the shaping.

25. The system of claim 17 wherein the flexible member is integrated with at least one of the CMUT or the ICs by at least one of coating, evaporating, sputtering or deposition.

26. A method of manufacturing an ultrasonic system, the method comprising:

providing a substrate with a capacitive micromachined ultrasonic transducer (CMUT);

patterning an insulation layer onto the substrate and the CMUT;

patterning a conductive layer onto a portion of the insulation layer, the conductive layer conductively connecting to the CMUT, wherein the CMUT, the insulation layer, and the conductive layer make up at least a portion of a flexible subassembly;

removing the flexible subassembly from the substrate; and shaping the flexible subassembly.

27. The method of claim 26, further comprising:

prior to removing the flexible subassembly from the substrate, forming a plurality of bonding pads on the flexible subassembly, the bonding pads conductively connecting to the conductive layer; and connecting an electrical integrated circuit to the plurality of bonding pads.

28. The method of claim 26, further comprising:

providing the substrate with an electrical integrated circuit (IC) on the substrate; and patterning the conductive layer to conductively connect to the IC.

29. The method of claim 26, wherein the providing the substrate with the CMUT comprises at least one of:

fabricating the CMUT on the substrate; or placing the CMUT on the substrate.

30. A method comprising:

disposing a capacitive micromachined ultrasonic transducer (CMUT) on a wafer;

applying an insulation layer of a first material and a conductive layer of a second material to the wafer and the CMUT;

removing the wafer to obtain a subassembly comprising:

the insulation layer, the conductive layer, and the CMUT; and shaping the subassembly to have at least one curved part.

31. The method as recited in claim 30, further comprising:

bonding an integrated circuit (IC) to the subassembly on a side of the insulation layer opposite to the CMUT; and electrically connecting the IC to the CMUT via the conductive layer.

32. The method as recited in claim 30, further comprising, prior to the applying the insulation layer, forming a trench in the wafer to define at least a portion of a boundary of the CMUT.

33. The method as recited in claim 30, further comprising, prior to the applying the insulation layer, disposing an integrated circuit on the wafer, wherein the applying the insulation layer includes applying the insulation layer to the integrated circuit.

* * * * *